United States Patent
Lee

(10) Patent No.: US 8,849,419 B2
(45) Date of Patent: Sep. 30, 2014

(54) SYSTEMS AND METHODS FOR MAKING AND USING ELECTRODES FOR ENHANCING STIMULATION PENETRATION OF PATIENT TISSUE

(75) Inventor: Dongchul Lee, Agua Dulce, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 304 days.

(21) Appl. No.: 13/237,674

(22) Filed: Sep. 20, 2011

(65) Prior Publication Data

US 2012/0078331 A1 Mar. 29, 2012

Related U.S. Application Data

(60) Provisional application No. 61/387,819, filed on Sep. 29, 2010.

(51) Int. Cl.
*A61N 1/05* (2006.01)
*A61N 1/36* (2006.01)
*A61N 1/375* (2006.01)

(52) U.S. Cl.
CPC ............... *A61N 1/05* (2013.01); *A61N 1/36182* (2013.01); *A61N 1/0553* (2013.01); *A61N 1/36153* (2013.01); *A61N 1/3752* (2013.01)
USPC .......................................... 607/116; 600/393

(58) Field of Classification Search
CPC ......... A61N 1/05; A61N 1/372; A61N 1/375; A61N 1/3752; A61N 1/0529; A61N 1/0531; A61N 1/0551; A61N 1/0553; H01R 2201/12
USPC ...................... 607/37–38, 115–117; 439/668; 600/377–378, 393
See application file for complete search history.

(56) References Cited

U.S. PATENT DOCUMENTS

| | | | |
|---|---|---|---|
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 | 7/2007 | Brase | |
| 7,437,193 B2 | 10/2008 | Parramon | |
| 7,672,734 B2 | 3/2010 | Anderson | |
| 7,761,165 B1 | 7/2010 | He | |
| 7,949,395 B2 | 5/2011 | Kuzma | |
| 7,974,706 B2 | 7/2011 | Moffitt | |
| 2003/0187490 A1* | 10/2003 | Gliner | 607/116 |
| 2005/0137665 A1* | 6/2005 | Cole | 607/116 |
| 2005/0165465 A1 | 7/2005 | Pianca | |
| 2007/0010862 A1* | 1/2007 | Osypka et al. | 607/115 |
| 2007/0118198 A1* | 5/2007 | Prager | 607/116 |
| 2007/0150036 A1 | 6/2007 | Anderson | |
| 2007/0219595 A1 | 9/2007 | He | |
| 2008/0071320 A1 | 3/2008 | Brase | |
| 2009/0118787 A1* | 5/2009 | Moffitt et al. | 607/45 |

\* cited by examiner

*Primary Examiner* — Carl H Layno
*Assistant Examiner* — Jessica Anthony
(74) *Attorney, Agent, or Firm* — Lowe Graham Jones PLLC; Patrick R. Turner

(57) ABSTRACT

A paddle lead assembly for providing electrical stimulation of patient tissue includes a paddle body having a plurality of electrodes. At least one of the plurality of electrodes defines a removed center portion. At least one lead body is coupled to the paddle body. At least one terminal is disposed on each of the at least one lead bodies.

18 Claims, 8 Drawing Sheets

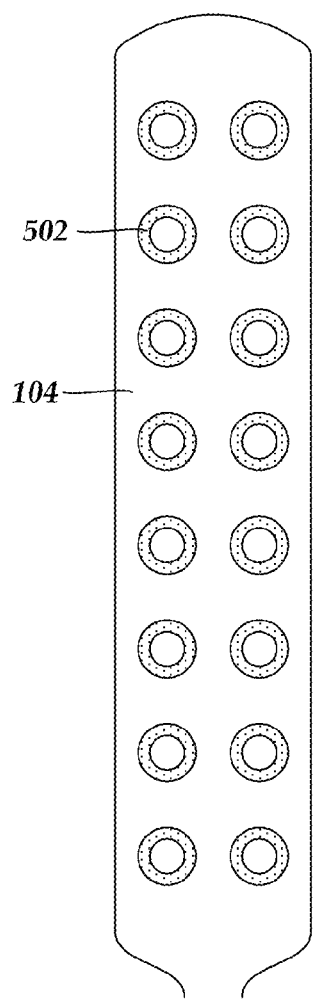
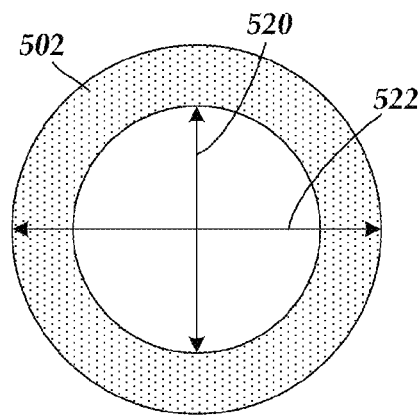
Fig. 5C
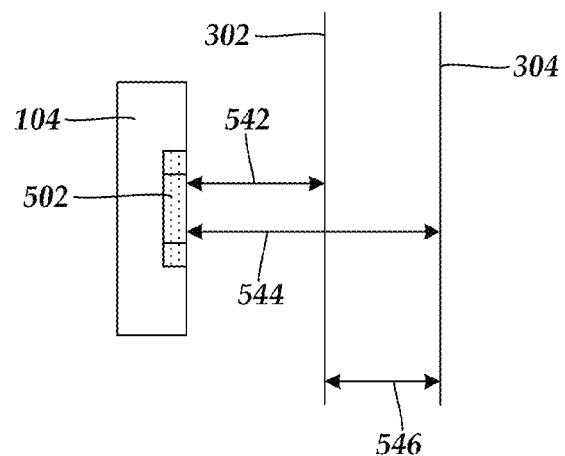
Fig. 5D
Fig. 5A
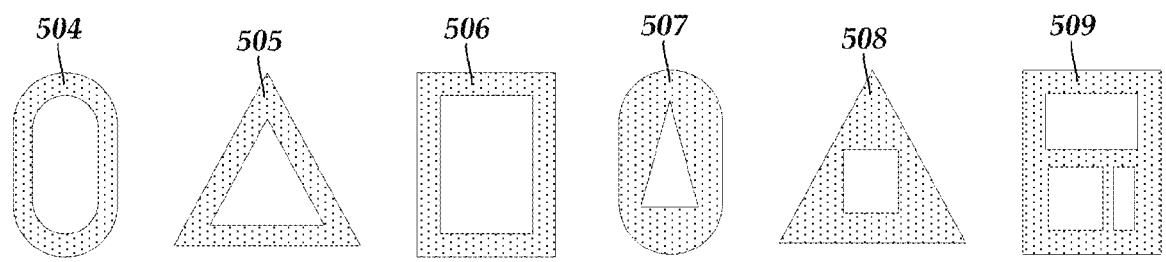
Fig. 5B

US 8,849,419 B2

SYSTEMS AND METHODS FOR MAKING AND USING ELECTRODES FOR ENHANCING STIMULATION PENETRATION OF PATIENT TISSUE

CROSS-REFERENCE TO RELATED APPLICATIONS

This application claims the benefit under 35 U.S.C. §119(e) of U.S. Provisional Patent Application Ser. No. 61/387,819 filed on Sep. 29, 2010, which is incorporated herein by reference.

FIELD

The present invention is directed to the area of implantable electrical stimulation systems and methods of making and using the systems. The present invention is also directed to implantable paddle leads that include electrodes configured and arranged for enhancing stimulation penetration of patient tissue, as well as methods of making and using the paddle leads, electrodes, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a paddle lead assembly for providing electrical stimulation of patient tissue includes a paddle body having a plurality of electrodes. At least one of the plurality of electrodes defines a removed center portion. At least one lead body is coupled to the paddle body. At least one terminal is disposed on each of the at least one lead bodies.

In another embodiment, an electrical stimulating system includes a paddle lead assembly. The paddle lead assembly includes a plurality of electrodes. At least one of the plurality of electrodes defines a removed center portion. At least one lead body is coupled to the paddle body. At least one terminal is disposed on each of the at least one lead bodies. A control module is configured and arranged to electrically couple to each of the at least one lead body. The control module includes a housing and an electronic subassembly disposed in the housing. At least one connector assembly is configured and arranged for receiving the at least one lead body. Each of the at least one connector assemblies includes a connector housing defining a port at a distal end of the connector housing. The port is configured and arranged for receiving a portion of one of the at least one lead bodies. At least one connector contact is disposed in the port. The at least one connector contact is configured and arranged to couple to the at least terminal disposed on one of the at least one lead bodies when one of the at least one lead bodies is inserted into the at least one connector assembly.

In yet another embodiment, a method for implanting a paddle lead includes inserting a paddle lead assembly into a patient. The paddle lead assembly includes a plurality of electrodes. At least one of the plurality of electrodes defines a removed center portion. At least one lead body is coupled to the paddle body. At least one terminal is disposed on each of the at least one lead bodies. A control module is provided. The control module includes a housing and an electronic subassembly disposed in the housing. The electronic subassembly includes a pulse generator. At least one connector assembly is provided. The at least one connector assembly includes a connector housing defining a port at a distal end of the connector housing. The port includes at least one connector contact. One of the at least one lead bodies is inserted into one of the at least one connector assemblies such that the at least one connector contact couples with the at least terminal disposed on one of the at least one lead bodies. Patient tissue is stimulated via the electrodes of the paddle lead assembly. The stimulation is provided by the pulse generator.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5A is a schematic top view of one embodiment of aperture electrodes disposed on the paddle body of FIG. 1, according to the invention;

FIG. 5B is a schematic top view of a plurality of embodiments of some aperture electrodes having different shapes from the aperture electrodes of FIG. 5A, according to the invention;

FIG. 5C is a schematic top view of one embodiment of one of the aperture electrodes of FIG. 5A, according to the invention;

FIG. 5D is a schematic cross-sectional view of one embodiment of one of the aperture electrodes of FIG. 5A stimulating both near tissue and far tissue, according to the invention;

DETAILED DESCRIPTION

The present invention is directed to the area of implantable electrical stimulation systems and methods of making and using the systems. The present invention is also directed to implantable paddle leads that include electrodes configured and arranged for enhancing stimulation penetration of patient tissue, as well as methods of making and using the paddle leads, electrodes, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; and U.S. Patent Applications Publication Nos. 2005/0165465, 2007/0150036; 2007/0219595; 2007/0239243; and 2008/0071320, all of which are incorporated by reference.

Figure 1:
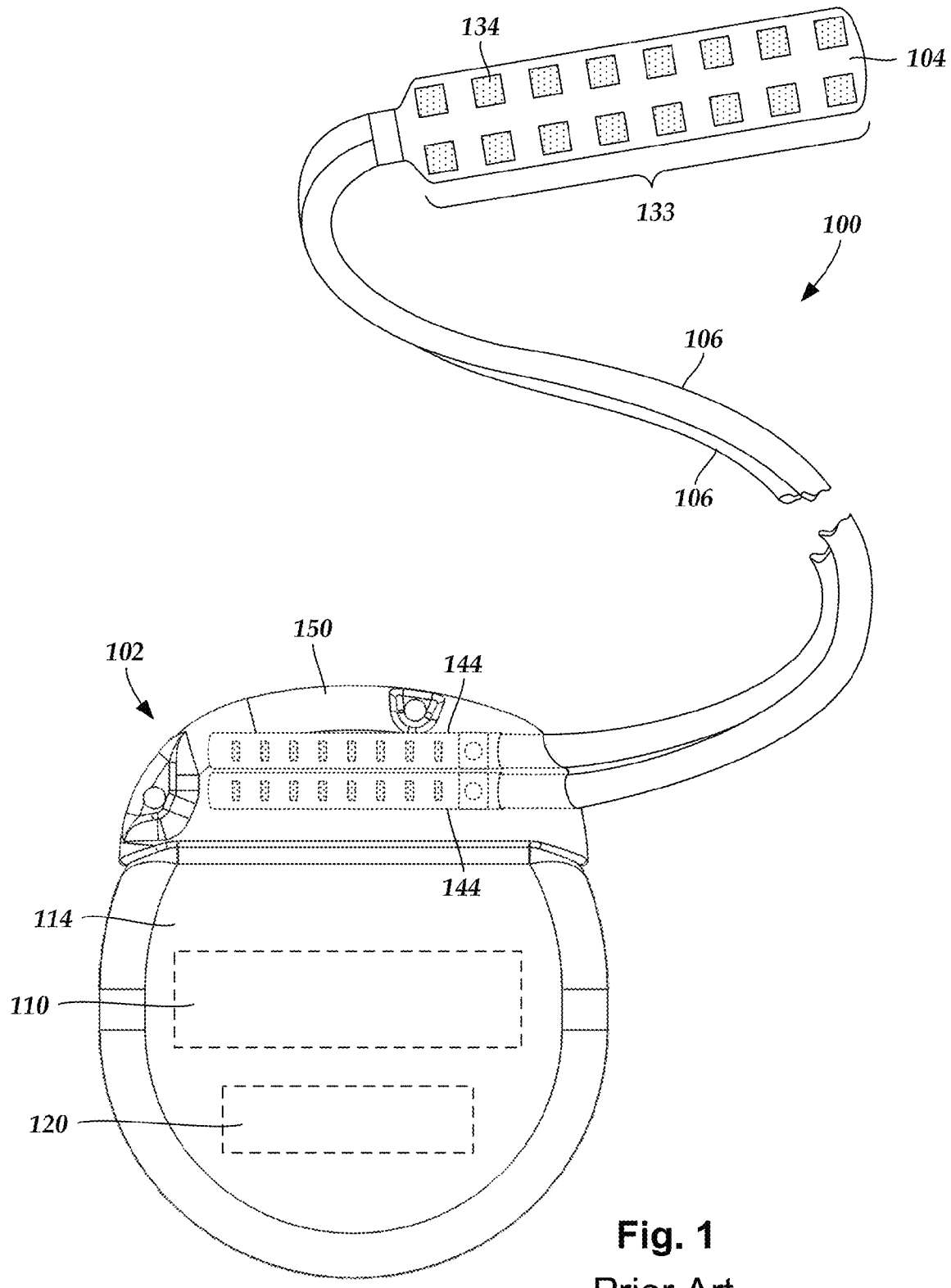
FIG. 1 is a schematic view of one embodiment of an electrical stimulation system that includes a lead body coupling a paddle body to a control module, the paddle body including a plurality of electrodes, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes a plurality of electrodes 134 that form an array of electrodes 133. The control module 102 typically includes an electronic subassembly 110 and an optional power source 120 disposed in a sealed housing 114.

The control module 102 typically includes one or more connector assemblies 144 (FIGS. 1-2B) into which the proximal end of the one or more lead bodies 106 can be plugged to make an electrical connection via connector contacts disposed in the connector assembly 144 and terminals (e.g., 210 in FIGS. 2A-2B and 236 of FIG. 2C) on each of the one or more lead bodies 106. The connector contacts are coupled to the electronic subassembly 110 and the terminals are coupled to the electrodes 134. In at least some embodiments, the connector assembly 144 is disposed in a header 150. In at least some embodiments, the header 150 provides a protective covering over the one or more connector assemblies 144. The header 150 may be formed using any suitable process including, for example, casting, molding (including injection molding), and the like. In addition, one or more lead extensions 224 (see FIG. 2C) can be disposed between the one or more lead bodies 106 and the control module 102 to extend the distance between the one or more lead bodies 106 and the control module 102.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, spinal cord stimulation, brain stimulation, neural stimulation, muscle activation via stimulation of nerves stimulating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: Platinum, Platinum Iridium, Palladium, Titanium nitride, or Rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals, (e.g., 210 in FIGS. 2A and 236 of FIG. 2C) are typically disposed at the proximal end of the one or more lead bodies 106 for connection to corresponding conductive contacts (e.g., 216 in FIGS. 2A-2B and 240 of FIG. 2C) in connector assemblies (e.g., 144 in FIGS. 1-2C) disposed on, for example, the control module 102 (or to other devices, such as conductive contacts on a lead extension, an operating room cable, a lead splitter, a lead adaptor, or the like). Conductive wires (not shown) extend from the terminals (e.g., 210 in FIGS. 2A and 236 of FIG. 2C) to the electrodes 134. Typically, one or more electrodes 134 are electrically coupled to a terminal (e.g., 210 in FIGS. 2A and 236 of FIG. 2C). In some embodiments, each terminal (e.g., 210 in FIGS. 2A and 236 of FIG. 2C) is only connected to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example; for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

In at least some embodiments, the one or more lead bodies 106 are coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead.

Figure 2A:
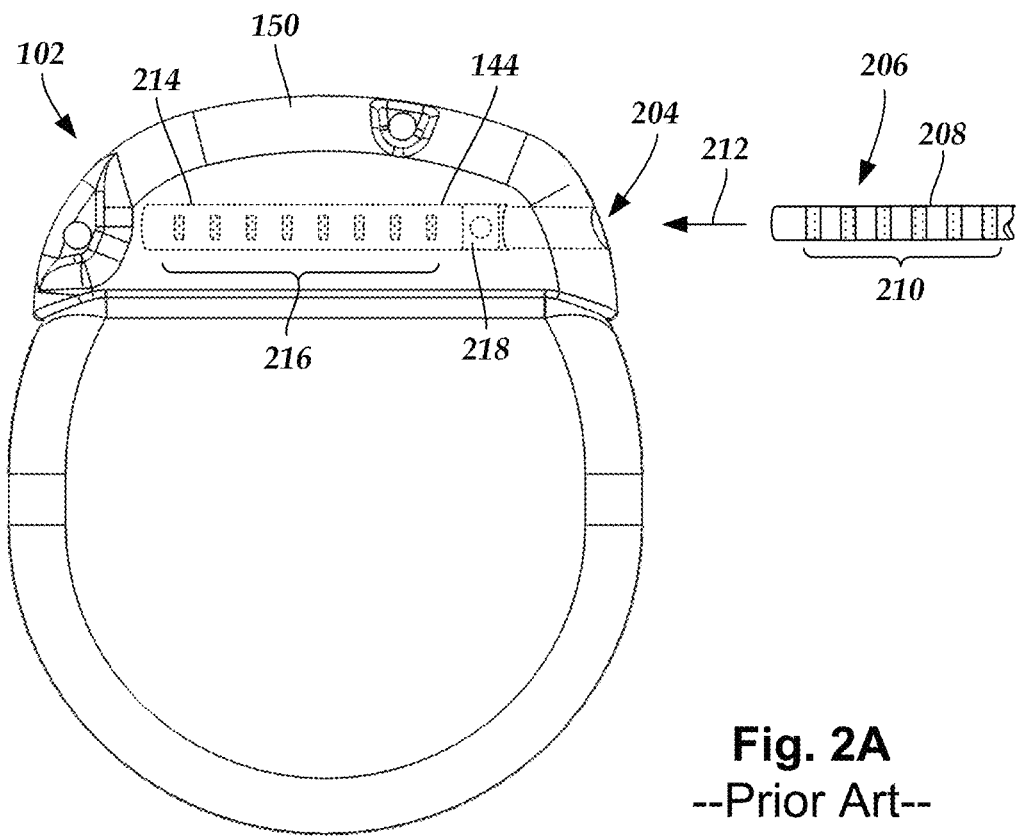
FIG. 2A is a schematic view of one embodiment of a proximal portion of a lead body configured and arranged for insertion into a connector assembly of the control module of FIG. 1, according to the invention.
Figure 2B:
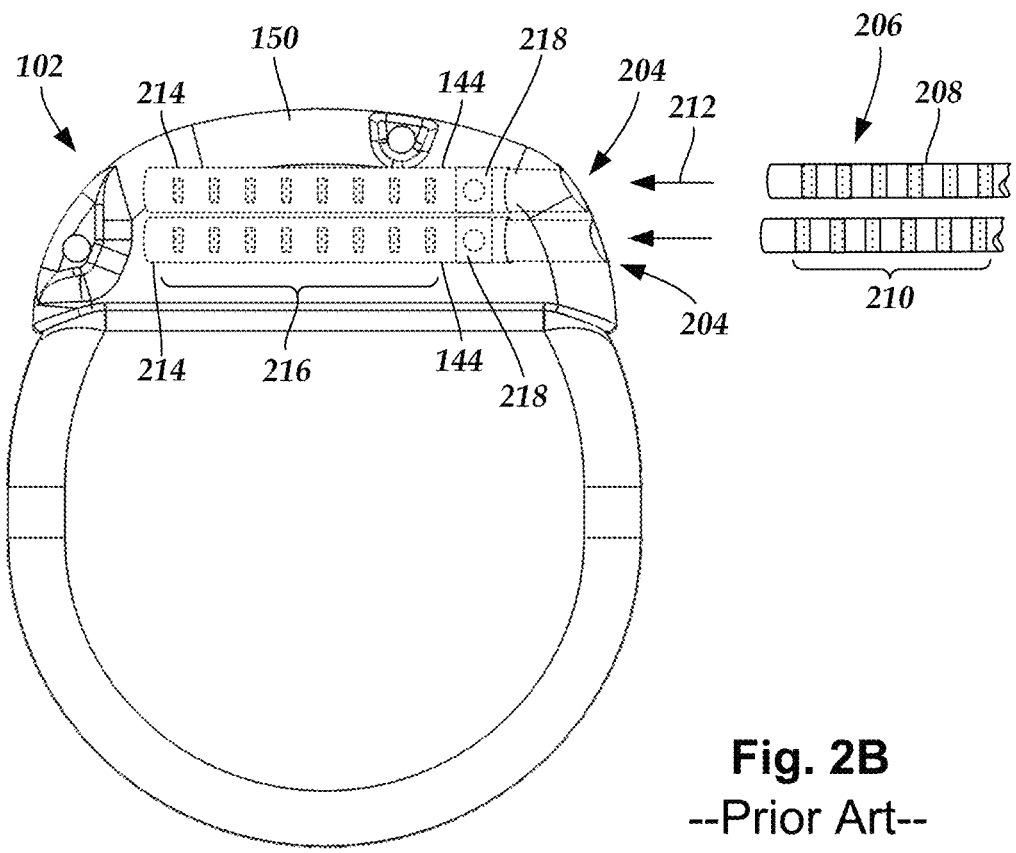
FIG. 2B is a schematic view of one embodiment of proximal portions of lead bodies configured and arranged for insertion into the control module of FIG. 1, according to the invention.

FIG. 2A is a schematic perspective view of one embodiment of the single connector assembly 144 disposed on the control module 102. FIG. 2B is a schematic perspective view of one embodiment of a plurality of connector assemblies 144 disposed on the control module 102. The proximal ends 206 of one or more leads 208 are shown configured and arranged for insertion to the control module 102. In FIGS. 2A and 2B, the one or more connector assemblies 144 are disposed in the header 150. In at least some embodiments, the header 150 defines one or more ports 204 into which a proximal end 206 of the one or more lead bodies 208 with terminals 210 can be inserted, as shown by directional arrows 212, in order to gain access to the connector contacts disposed in the one or more connector assemblies 144.

The one or more connector assemblies 144 each include a connector housing 214 and a plurality of connector contacts 216 disposed therein. Typically, the connector housing 214 defines a port (not shown) that provides access to the plurality of connector contacts 216. In at least some embodiments, one or more of the connector assemblies 144 further includes a retaining element 218 configured and arranged to fasten the corresponding lead body 208 to the connector assembly 144 when the lead body 208 is inserted into the connector assembly 144 to prevent undesired detachment of the lead body 208 from the connector assembly 144. For example, the retaining element 218 may include an aperture through which a fastener (e.g., a set screw, pin, or the like) may be inserted and secured against an inserted lead body or lead extension.

When the one or more lead bodies 208 are inserted into the one or more ports 204, the connector contacts 216 can be aligned with the terminals 210 disposed on the one or more lead bodies 208 to electrically couple the control module 102 to the electrodes (134 of FIG. 1) disposed at a distal end of the one or more lead bodies 208. Examples of connector assemblies in control modules are found in, for example, U.S. Pat. No. 7,244,150 and U.S. Patent Application Publication No. 2008/0071320, which are incorporated by reference.

Figure 2C:
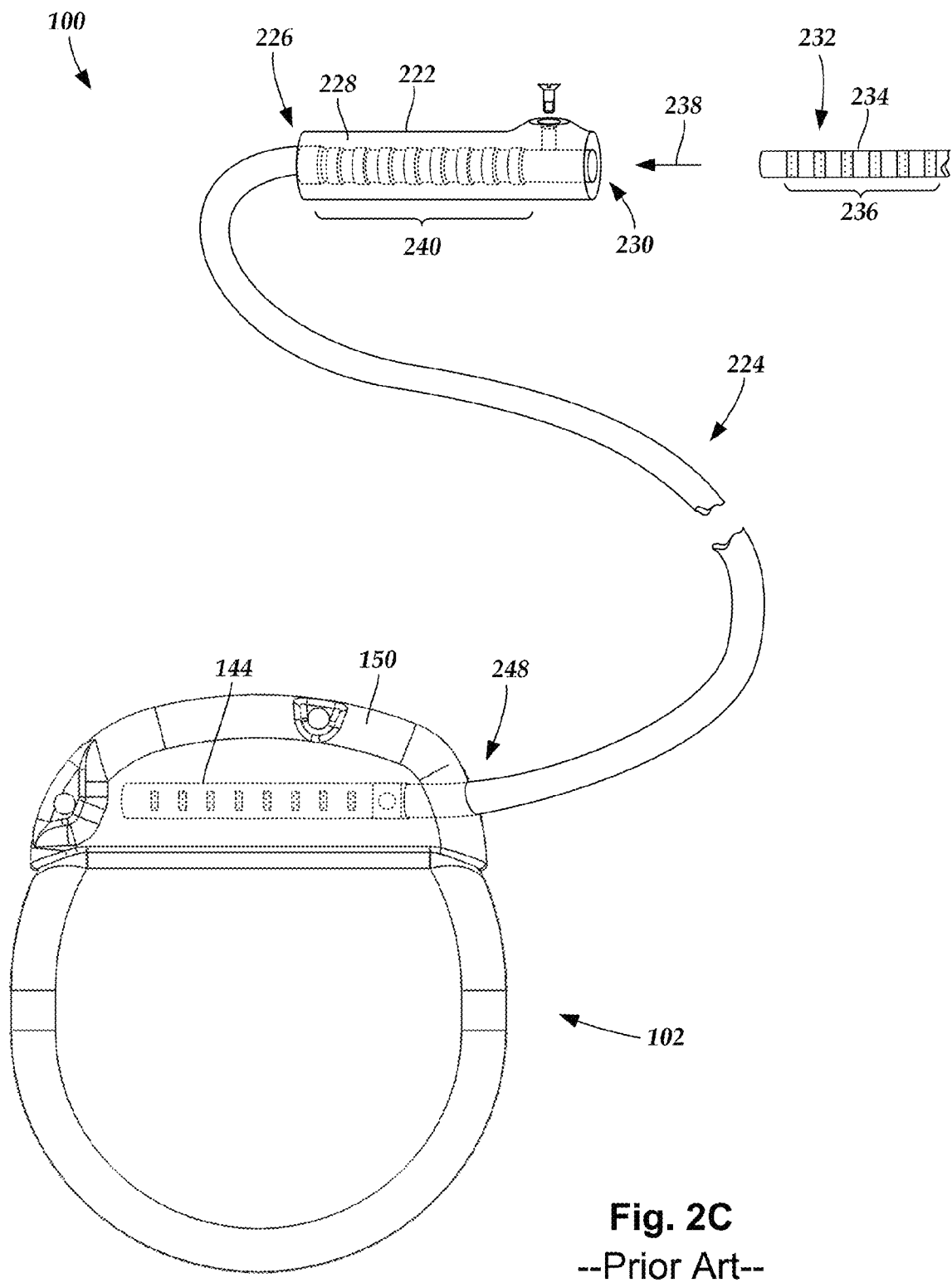
FIG. 2C is a schematic view of one embodiment of a proximal portion of a lead body configured and arranged for insertion into a lead extension which, in turn, is configured and arranged for insertion into the control module of FIG. 1, according to the invention.

In FIG. 2C, a lead extension connector assembly 222 is disposed on a lead extension 224. The lead extension connector assembly 222 is shown disposed at a distal end 226 of the lead extension 224. The lead extension connector assembly 222 includes a contact housing 228. The contact housing 228 defines at least one port 230 into which a proximal end 232 of a lead body 234 with terminals 236 can be inserted, as shown by directional arrow 238. The lead extension connector assembly 222 also includes a plurality of connector contacts 240. When the lead body 234 is inserted into the port 230, the connector contacts 240 disposed in the contact housing 228 can be aligned with the terminals 236 on the lead body 234 to electrically couple the lead extension 224 to the electrodes (134 of FIG. 1) disposed at a distal end (not shown) of the lead body 234.

In at least some embodiments, the proximal end of a lead extension is similarly configured and arranged as a proximal end of a lead body. The lead extension 224 may include a plurality of conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a lead extension connector assembly disposed in another lead extension. In other embodiments (as shown in FIG. 2C), the proximal end 248 of the lead extension 224 is configured and arranged for insertion into the connector assembly 144 disposed on the control module 102.

It may be useful to stimulate a target tissue site that is not immediately adjacent to the paddle body 104 ("far tissue"). Typically, the farther away the far tissue from the electrodes 134, the higher the level of stimulation amplitude needed to effectively stimulate the far tissue. Increasing the level of stimulation amplitude, however, may be detrimental to (e.g., over-stimulate) tissue that is closer to the paddle body 104 than the far tissue ("near tissue"). Thus, the distance from the electrodes 134 to the far tissue typically does not exceed a distance that enables effective stimulation of the far tissue without over-stimulating near tissue.

Figure 3A:
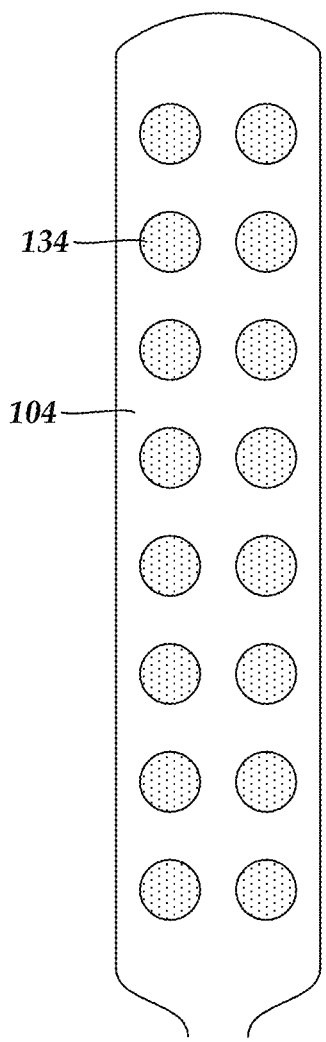
FIG. 3A is a schematic top view of one embodiment of the electrodes of FIG. 1 disposed on the paddle body of FIG. 1, according to the invention.
Figure 3B:
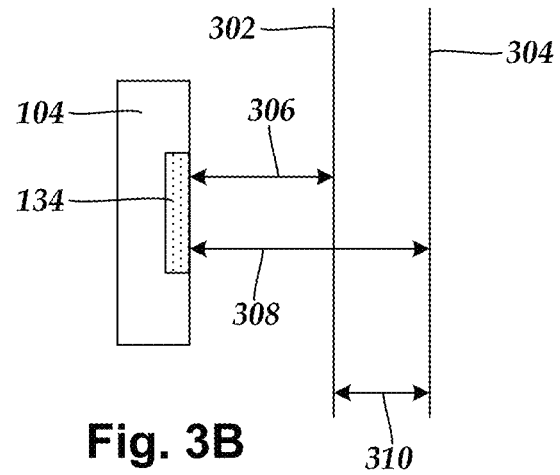
FIG. 3B is a schematic cross-sectional view of one embodiment of one of the electrodes of FIG. 1 stimulating both near tissue and far tissue, according to the invention.

FIG. 3A is a schematic top view of one embodiment of the electrodes 134 disposed on the paddle body 104. In FIG. 3A, the electrodes 134 are formed into a circular shape. FIG. 3B is a schematic cross-sectional view of one embodiment of one of the circular electrodes 134 stimulating both near tissue 302 and far tissue 304. In FIG. 3B and in other figures, the near tissue 302 and the far tissue 304 are shown as lines representing excitable tissue, such as nerve fibers. It will be understood that the near tissue 302 and the far tissue 304 may be any tissue within the patient.

In FIG. 3B, the distance 306 between the electrode 134 and the near tissue 302 is less than the distance 308 between the electrode 134 and the far tissue 304 by a given distance 310. In at least some embodiments, the distance 308 between the electrode 134 and the far tissue 304 is no greater than 10 mm, 9 mm, 8 mm, 7 mm, 6 mm, 5 mm, 4 mm, 3 mm, 2 mm, 1 mm, or less. In at least some embodiments, the distance 306 between the electrode 134 and the near tissue 302 is at least 100 μm. In at least some embodiments, the distance 306 between the electrode 134 and the near tissue 302 is no greater than 5 mm, 4 mm, 3 mm, 2 mm, 1 mm, or less. In at least some embodiments, the distance 310 is at least 1 mm, 2 mm, 3 mm, 4 mm, 5 mm, 6 mm, or more.

Figure 3C:
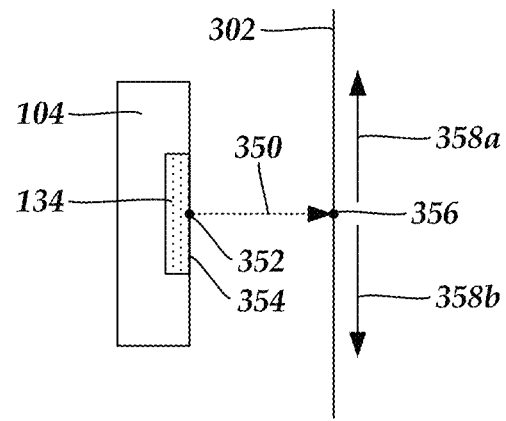
FIG. 3C is a schematic cross-sectional view of one embodiment of a normal stimulation line propagating from a center of the electrode of FIG. 3B, the stimulation line contacting a portion of the near tissue of FIG. 3B, according to the invention.

FIG. 3C is a schematic cross-sectional view of one embodiment of one of the circular electrodes 134 stimulating near tissue 302. In FIG. 3C, a dotted line 350 represents stimulation propagating outward from a center 352 of the electrode 134 in a direction that is normal to a face 354 of the electrode 134. In FIG. 3C, a dot 356 on the near tissue 302 represents the portion of the near tissue 302 most-directly stimulated by the center 352 of the electrode 134 (e.g., on the normal line 350 from the center 352 of the electrode). The opposing arrows 358a and 358b represent distances outward along the near tissue 302 in two opposing directions from the dot 356 (e.g., along opposing radii parallel with the face 354 of the electrode 134).

When stimulating the near tissue 302 with the electrode 134, the received stimulation amplitude along the near tissue 302 may be strongest at the portion 356 of the near tissue 302. The stimulation amplitude may lessen along the arrows 358a and 358b. It will be understood that a similar stimulation arrangement may exist for the far tissue 304 when the far tissue 304 is stimulated by the electrode 134.

Figure 4A:
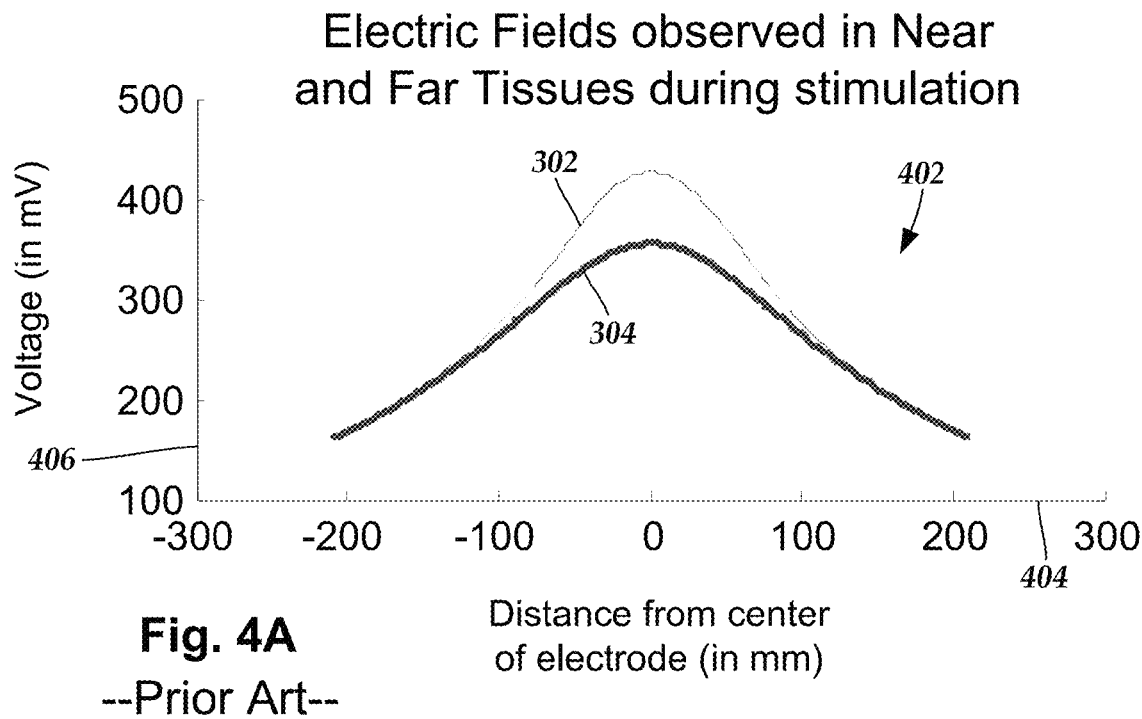
FIG. 4A is a graph showing electric fields observed in the near and far tissues of FIG. 3B during stimulation using the electrodes of FIG. 1, according to the invention.
Figure 4B:
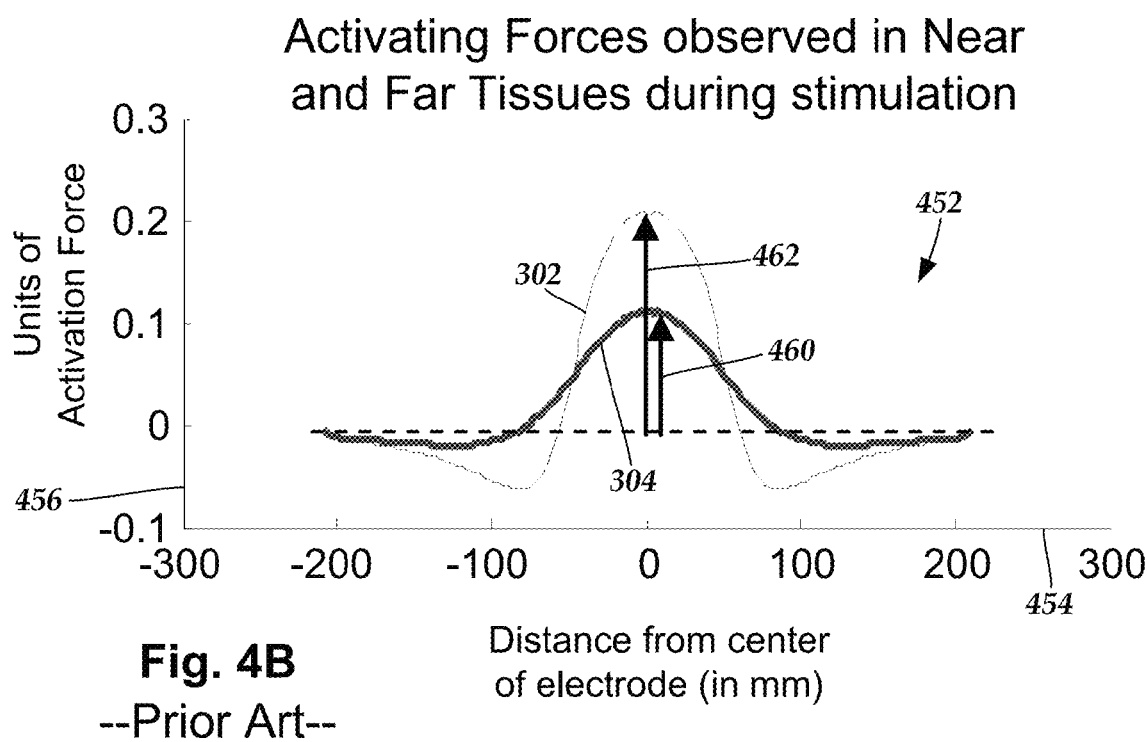
FIG. 4B is a graph showing activating forces observed in the near and far tissues of FIG. 3B during stimulation using the electrodes of FIG. 1, according to the invention.

FIGS. 4A and 4B show graphs of electrical fields and activation forces experienced by the near tissue 302 and the far tissue 304 for the arrangement shown in FIG. 3B when stimulated by the electrodes 134 at a given stimulation amplitude. FIG. 4A is a graph 402 showing electric fields observed in near tissue 302 and far tissue 304 during stimulation using the electrode 134. The x-axis 404 defines distances outward in two opposing directions from the portion 356 of the stimulated tissue that corresponds to the center 352 of the electrode 134 (e.g., along an axis represented in FIG. 3C by opposing arrows 356a and 356b). The y-axis 406 defines the electrical potential of the electric field generated by the electrode 134 as a function of the distances in the two opposing directions from the center of the electrode 134. As shown in the graph 402, the highest electrical potential for the near tissue 302 is larger than the highest electrical potential for the far tissue 304. For both near tissue 302 and far tissue 304, the highest electrical potential of the electric field generated by the electrode 134 is at the center of the electrode 134. The electrical potential experienced by the near tissue 302 drops more steeply from the center of the electrode 134 than the electrical potential experienced by the far tissue 304.

Generating an electric field at the location of patient tissue, such as nerve fibers, may cause an action potential to be formed along the tissue, thereby initiating an intracellular process. Formation of action potentials in tissue can be related to depolarization of nerve tissue, which corresponds to a positive direction in an "activation function". An activation function is a second difference of extracellular voltage at nodes of Ranvier along myelinated nerve fibers. The unit of activating function is arbitrary, but can be used to show relative force generated to depolarize nerve tissues. Thus, an activating function is a first order of estimation about nerve depolarization, which is proportional to the likelihood of action potential generation. Accordingly, activation functions can be used to compare relative activation forces experienced by different tissues (e.g., near tissue 302 and far tissue 304).

FIG. 4B is a graph 452 showing activating forces observed in the near tissue 302 and the far tissue 304 during stimulation using the electrodes 134 at the given stimulation amplitude used in FIG. 4A. As mentioned above, the near tissue 302 is positioned closer to the electrode 134 than the far tissue 304. The x-axis 454 defines distances outward in two opposing directions from the portion 356 of the stimulated tissue that corresponds to the center 352 of the electrode 134 (e.g., along an axis represented in FIG. 3C by opposing arrows 356a and 356b). The y-axis 456 defines the strength of the activation force of the electric field generated by the electrode 134 as a function of the distance outward in the two opposing directions from the center of the electrode 134.

The peak point of activation force for the far tissue 304 is shown as an arrow 460. The peak point of activation force for the near tissue 302 is shown as an arrow 462. As shown in the graph 452, the peak points 462, 460 of activation forces for the near and far tissues 302 and 304, respectively, both occur at the portion 356 of the stimulated tissue that corresponds to the center 352 of the electrode 134. As shown in FIG. 4B, the peak point 462 of activation force for the far tissue 304 has a value that is about twice the value of the peak point 460 of activation force for the near tissue 302. Thus, the ratio of the peak point 460 of activation force for the far tissue 304 to the peak point 462 of activation force for the near tissue 302 is about two. Accordingly, the near tissue 302 is experiencing about twice the activation force as the far tissue 304.

As described herein, aperture electrodes may provide enhanced penetration of patient tissue such that, given the activation force for far tissue 304, the relative strength of the activation force for near tissue 302 is less for the aperture electrode than for the electrode 134. Thus, in at least some embodiments, employing aperture electrodes enables the operational distance between the aperture electrodes and the far tissue (distance 546 in FIG. 5D) to be increased from the corresponding operational distance between the electrodes 134 and the far tissue (distance 310 in FIG. 3B) without over-stimulating the near tissue 302. Accordingly, employing aperture electrodes may enable the far tissue 304 to be stimulated without over-stimulating the near tissue 302 at a distance that is greater than would be obtainable by employing the electrodes 134.

In at least some embodiments, aperture electrodes include at least one removed portion (e.g., at least one aperture) at the center of the aperture electrode. For example, in at least some embodiments, aperture electrodes are ring-shaped. In at least some embodiments, removal of the center of an electrode may change the electric field, as well as the activation force, experienced by near tissue without significantly changing the electric field or the activation force experienced by far tissue. In at least some embodiments, removal of the center of an electrode may reduce the electric field, as well as the activation force, experienced by near tissue without significantly changing the electric field or the activation force experienced by far tissue. Thus, employing aperture electrodes may increase the distance of stimulated far tissue from the aperture electrodes, as compared to the electrodes 134, without over-stimulating near tissue.

FIG. 5A is a schematic top view of one embodiment of aperture electrodes 502 disposed on the paddle body 104. In FIG. 5A, the aperture electrodes 502 are shown as being circular. Alternately (as shown in FIG. 5B), the aperture electrodes 502 can be any suitable shape with a removed center including, for example, oval-shaped 504, triangular 505, rectangular 506, or the like. The apertures can be any suitable shape. In FIG. 5B, electrodes 507 and 508 are shown having apertures that are different shapes than outer surfaces of the electrodes 507 and 508. The aperture electrodes can have any suitable number of apertures. For example, in FIG. 5B the aperture electrode 509 is shown defining a plurality of apertures.

FIG. 5C is a schematic top view of one embodiment of one of the ring-shaped aperture electrodes 502. The aperture electrode 502 has an inner diameter 520 and an outer diameter 522. The aperture electrodes 502 can be any suitable size. For example, the aperture electrode 502 can have an outer diameter 522 of at least 2 mm, 3 mm, 4 mm, 5 mm, 6 mm, 7 mm, 8 mm, 9 mm, 10 mm, or more. The inner diameter 520 can be any suitable length including, for example, at least 1 mm, 2 mm, 3 mm, 4 mm, 5 mm, 6 mm, 7 mm, 8 mm, or more. In at least some embodiments, the inner diameter 520 is at least 20%, 30%, 40%, 50%, 60%, 70%, or 80% as large as the inner diameter 522.

FIG. 5D is a schematic cross-sectional view of one embodiment of one of the ring-shaped aperture electrodes 502 stimulating both near tissue 302 and far tissue 304. In FIG. 5l), the distance 542 between the electrode 502 and the near tissue 302 is less than the distance 544 between the electrode 502 and the far tissue 304 by a given distance 546. The distances 542, 544, and 546 are equal to the corresponding distances 306, 308, and 310 of FIG. 3B.

Figure 6A:
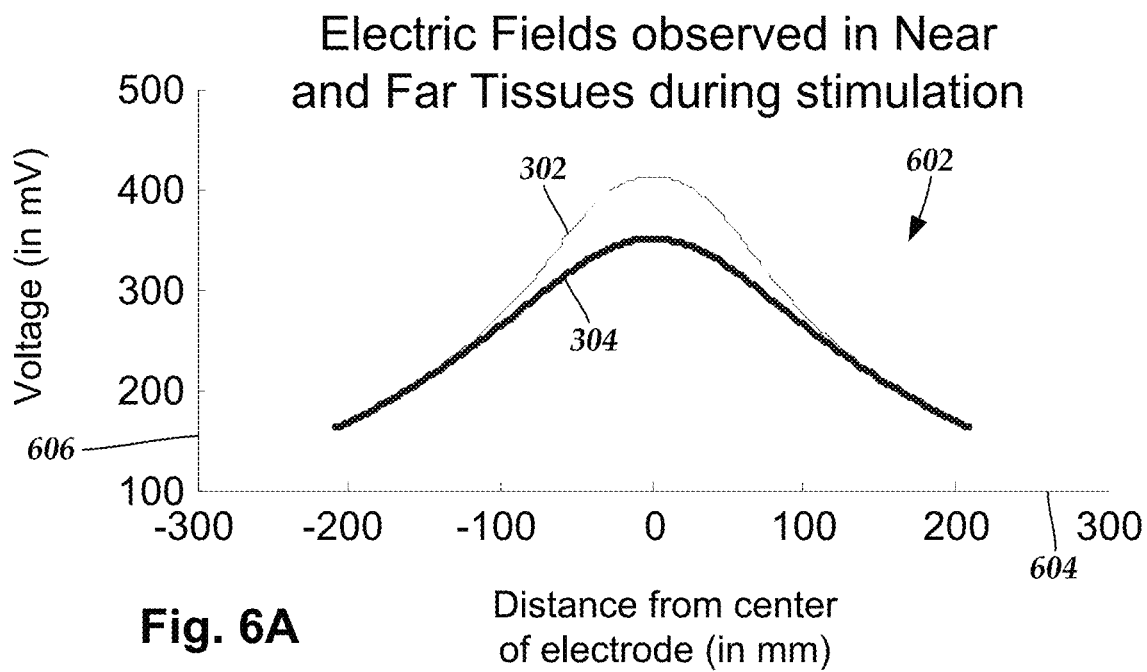
FIG. 6A is a graph showing electric fields observed in the near and far tissues of FIG. 5D during stimulation using the aperture electrodes of FIG. 5A, according to the invention.
Figure 6B:
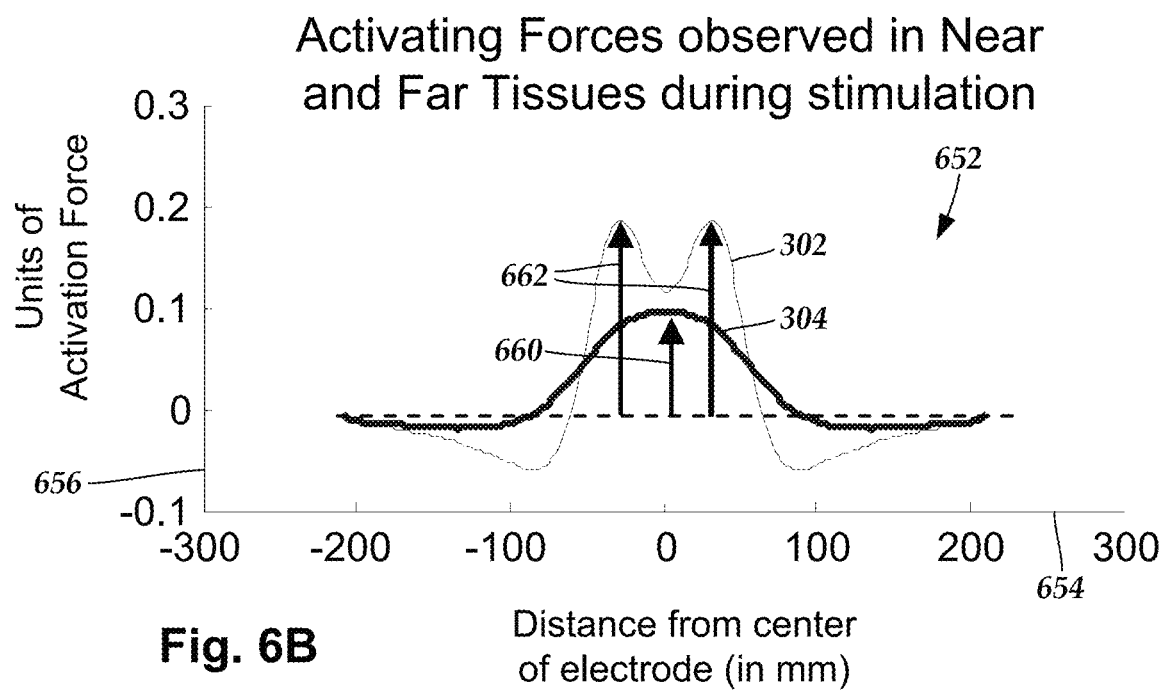
FIG. 6B is a graph showing activating forces observed in the near and far tissues of FIG. 5D during stimulation using the aperture electrodes of FIG. 5A, according to the invention.

FIGS. 6A and 6B show graphs of electrical fields and activation forces experienced by the near tissue 302 and the far tissue 304 for the arrangement shown in FIG. 5D when stimulated by the aperture electrodes 502. FIG. 6A is a graph 602 showing electric fields observed in the near tissue 302 and far tissue 304 during stimulation using one of the aperture electrodes 502. The x-axis 604 defines distances outward in two opposing directions from the portion of the stimulated tissue that corresponds to the center of the electrode 502 (e.g., along an axis represented in FIG. 3C by opposing arrows 356*a* and 356*b*). The y-axis 606 defines the voltage of the electric field generated by the aperture electrode 502 as a function of the distances in the two opposing directions from the center of the aperture electrode 502.

As shown in the graph 602, the highest electrical potential experienced by the near tissue 302 is larger than the highest electrical potential experienced by the far tissue 304. Additionally, for both the near tissue 302 and the far tissue 304, the highest electrical potential of the electric field generated by the aperture electrode 602 is at the center of the aperture electrode 502. In FIG. 4A, the near tissue 302 is shown experiencing an electrical potential that drops steeply from the center of the electrode 134. In contrast, in FIG. 6A, the near tissue 302 is shown experiencing an electrical potential that is relatively flat over a larger distance of the aperture electrode 502 than for the electrode 134. In at least some embodiments, the near tissue 302 experiences a relatively flat electrical potential along at least half of the outer diameter 522 of the aperture electrode 502. In at least some embodiments, the near tissue 302 experiences a relatively flat electrical potential along substantially the entire outer diameter 522 of the aperture electrode 502. In at least some embodiments, the near tissue 302 experiences a relatively flat electrical potential along the entire outer diameter 522 of the aperture electrode 502.

FIG. 6B is a graph 652 showing activating forces observed in the near tissue 302 and the far tissue 304 during stimulation using the aperture electrodes 502. As mentioned above, the near tissue 302 is positioned closer to the electrode 134 than the far tissue 304. The x-axis 654 defines distances outward in two opposing directions from the portion of the stimulated tissue that corresponds to the center of the aperture electrode 502 (e.g., along an axis represented in FIG. 3C by opposing arrows 356*a* and 356*b*). The y-axis 656 defines the strength of the activation force of the electric field generated by the aperture electrode 502 as a function of distances outward in two opposing directions from the center of the aperture electrode 502. A peak point 660 of activation force for the far tissue 304 occurs at the center of the aperture electrode 502 at about the same magnitude and shape as for the far tissue 304 shown in FIG. 4A, potentially indicating that there is no significant difference between stimulating the far tissue 304 with either the electrodes 134 or the aperture electrodes 502.

The near tissue 302, however, experiences a different activation force from stimulation by the aperture electrode 502 than from the electrode 134. In FIG. 6B, the activation force experienced by the near tissue 302 includes multiple peak points, shown in FIG. 6B as arrows 662. Additionally, as shown in FIG. 6B, the peak points 662 of activation force for the far tissue 304 have values that are less than twice the value of the peak point 660 of activation force for the near tissue 302. In at least one experiment, computer modeling has indicated that the ratio of the peak point 460 of activation force for the far tissue 304 to the peak point 462 of activation force for the near tissue 302 from stimulation by the electrode 134 (see FIG. 4B) was less than the ratio of the peak points 660 of activation force for the far tissue 304 to the peak point 662 of activation force for the near tissue 302 from stimulation by the aperture electrode 502 (as shown in FIG. 6B). Thus, at a given distance, when the far tissue 304 is stimulated by the aperture electrodes 502, the activation force experienced by the near tissue 302 is less than a corresponding activation force experienced by the near tissue 302 when the far tissue 304 is stimulated by the electrodes 134. Accordingly, when employing aperture electrodes 502 it may be possible to increase the stimulation distance between the aperture electrodes 502 and the far tissue 304, as compared to the electrodes 134, without over-stimulating the near tissue 302.

Figure 7:
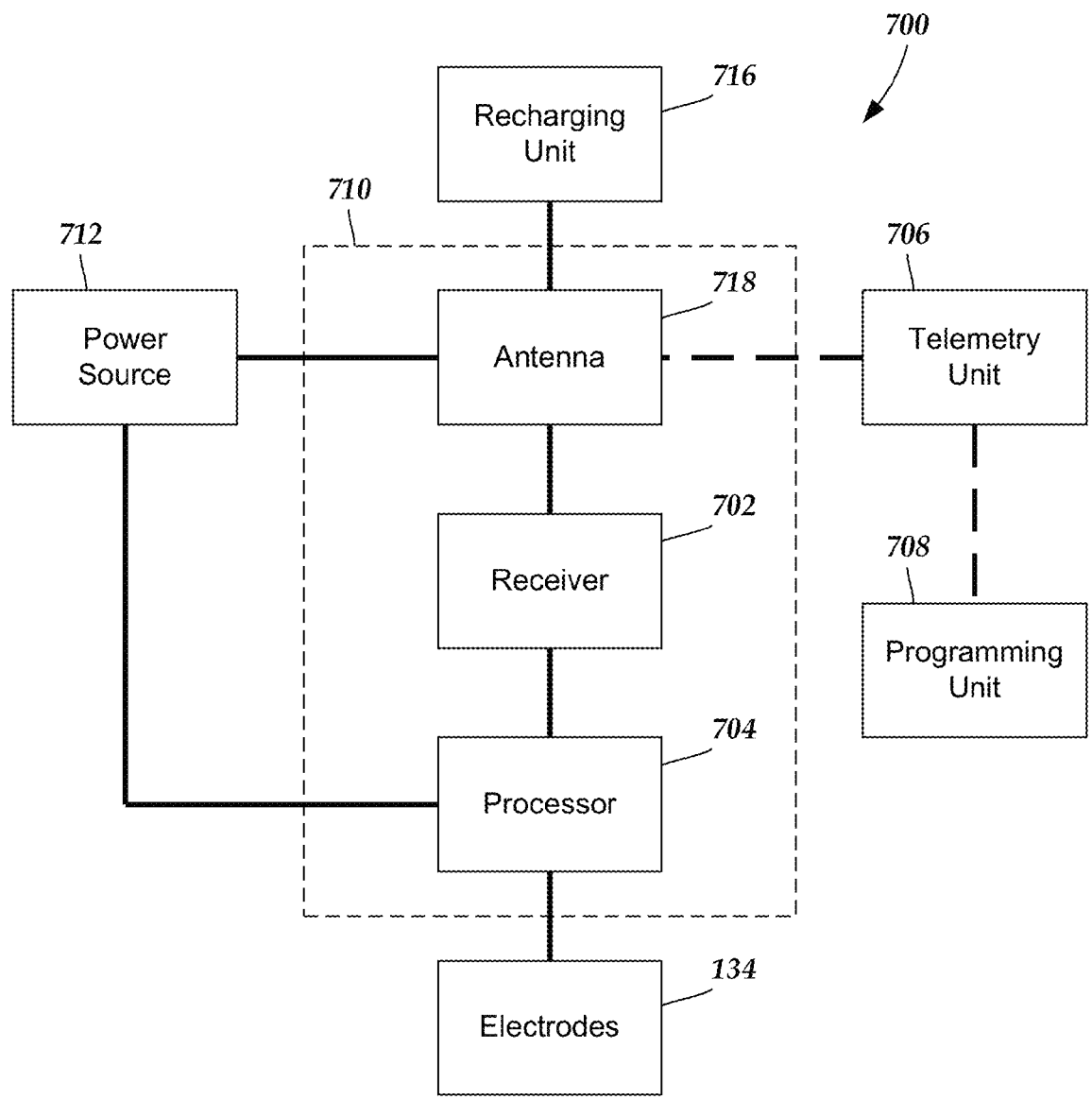
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally, included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A paddle lead assembly for providing electrical stimulation of patient tissue, the paddle lead assembly comprising:
    a paddle body;
    a plurality of electrodes disposed along the paddle body, wherein at least one electrode of the plurality of electrodes defines a removed center portion, wherein the at least one of the plurality of electrodes with the removed center portion has an outer surface defined by an outer edge of the at least one of the plurality of electrodes and an inner surface defined by the removed center portion, and wherein a shape of the outer surface is different from a shape of the inner surface;
    at least one lead body coupled to the paddle body;
    at least one terminal disposed on each of the at least one lead body; and
    a plurality of conductive wires coupling each of the plurality of electrodes to the at least one terminal.

2. The paddle lead assembly of claim 1, wherein the outer surface of the at least one of the plurality of electrodes with the removed center portion is circular.

3. The paddle lead assembly of claim 1, wherein the outer surface of the at least one of the plurality of electrodes with the removed center portion is one of oval-shaped, rectangular, or triangular.

4. The paddle lead assembly of claim 1, wherein each of the at least one of the plurality of electrodes with the removed center portion has an inner diameter and an outer diameter.

5. The paddle lead assembly of claim 4, wherein the inner diameter is at least half as large as the outer diameter.

6. The paddle lead assembly of claim 1, wherein the paddle body comprises at least sixteen electrodes.

7. The paddle lead assembly of claim 1, wherein the paddle body is formed from at least one of silicon or polyurethane.

8. An electrical stimulating system comprising:
    the paddle lead assembly of claim 1;
    a control module configured and arranged to electrically couple to each of the at least one lead body, the control module comprising
        a housing, and
        an electronic subassembly disposed in the housing; and
    at least one connector assembly configured and arranged for receiving the at least one lead body, each of the at least one connector assemblies comprising
        a connector housing defining a port at a distal end of the connector housing, the port configured and arranged for receiving a portion of one of the at least one lead bodies, and
        at least one connector contact disposed in the port, the at least one connector contact configured and arranged to couple to the at least terminal disposed on one of the at least one lead bodies when one of the at least one lead bodies is inserted into the at least one connector assembly.

9. The electrical stimulation system of claim 8, wherein the at least one of the electrode with the removed center portion is ring-shaped.

10. The electrical stimulation system of claim 8, wherein the connector assembly is disposed on the control module.

11. The electrical stimulation system of claim 8, further comprising a lead extension having a distal end and a proximal end, wherein the connector assembly is disposed on the distal end of the lead extension and the proximal end of the lead extension is configured and arranged to couple with the control module.

12. The electrical stimulation system of claim 11, wherein the at least one connector assembly is a first at least one connector assembly, and wherein the a second at least one connector assembly is disposed on the control module, the second at least one connector assembly configured and arranged to receive the proximal end of the lead extension.

13. The paddle lead assembly of claim 1, wherein each remaining electrode of the plurality of electrodes is disposed along the paddle body external to the removed center portion of the at least one electrode.

14. A method for implanting a paddle lead, the method comprising:
inserting the paddle lead assembly of claim 1 into a patient;
providing a control module, the control module comprising a housing and an electronic subassembly disposed in the housing, the electronic subassembly comprising a pulse generator;
providing at least one connector assembly, the at least one connector assembly comprising a connector housing defining a port at a distal end of the connector housing, the port comprising at least one connector contact;
inserting one of the at least one lead bodies into one of the at least one connector assemblies such that the at least one connector contact couples with the at least terminal disposed on one of the at least one lead bodies; and
stimulating patient tissue via the electrodes of the paddle lead assembly, the stimulation provided by the pulse generator.

15. The method of claim 14, wherein inserting one of the at least one lead bodies into one of the at least one connector assemblies comprises inserting one of the at least one lead bodies into one of the at least one connector assemblies disposed on the control module.

16. The method of claim 14, further comprising providing a lead extension, the lead extension having a proximal end and a distal end, wherein the proximal end of the lead extension is coupled to the control module.

17. The method of claim 16, wherein inserting one of the at least one lead bodies into one of the at least one connector assemblies comprises inserting one of the at least one lead bodies into one of the at least one connector assemblies disposed on the distal end of the lead extension.

18. A paddle lead assembly for providing electrical stimulation of patient tissue, the paddle lead assembly comprising:
a paddle body;
a plurality of electrodes disposed along the paddle body, wherein at least one electrode of the plurality of electrodes defines a plurality of removed center portions, wherein the at least one of the plurality of electrodes with the plurality of removed center portions has an outer surface defined by an outer edge of the at least one of the plurality of electrodes and a plurality of inner surfaces defined by the plurality of removed center portions, and wherein a shape of the outer surface is different from a shape of at least one of the plurality of inner surfaces;
at least one lead body coupled to the paddle body;
at least one terminal disposed on each of the at least one lead body; and
a plurality of conductive wires coupling each of the plurality of electrodes to the at least one terminal.

* * * * *